United States Patent [19]
Hardy

[11] Patent Number: 6,010,874
[45] Date of Patent: Jan. 4, 2000

[54] EARLY ONSET ALZHEIMER'S DISEASE GENE AND GENE PRODUCTS

[75] Inventor: John A. Hardy, St. Augustine, Fla.

[73] Assignee: University of South Florida, Tampa, Fla.

[21] Appl. No.: 08/670,964

[22] Filed: Jun. 26, 1996

Related U.S. Application Data

[60] Provisional application No. 60/001,142, Jul. 13, 1995, and provisional application No. 60/001,501, Jul. 18, 1995.

[51] Int. Cl.$^7$ .............................. C12P 21/00; C12N 1/21; C12N 15/00; C07K 14/46
[52] U.S. Cl. ................. 435/69.1; 435/252.3; 435/320.1; 536/23.5; 530/350
[58] Field of Search ............................... 435/69.1, 252.3, 435/320.1; 536/23.5; 530/350

[56] References Cited

U.S. PATENT DOCUMENTS 5,449,604   9/1995   Schellenberg et al. ..................... 435/6

OTHER PUBLICATIONS

Hillier et al. GenBank. Accession No. R05907. Apr. 3, 1995.
Mullan, M. et al., "A locus for familial early–onset Alzheimer's disease on the long arm of chromosome 14, proximal to the α1–antichymotrypsin gene", Nature Genet., 1992, 2:340–342.
Mullan, M. et al., "Clinical Features of Early Onset, Familial Alzheimer's Disease Linked to Chromosome 14", Am. J. of Med. Genet., 1995, 60:44–52.
Schellenberg, G.D. et al., "Chromosome 14 and Late–Onset Familial Alzheimer Disease (FAD)", Am. J. Hum. Genet., 1993, 53:619–628.
Schellenberg, G.D. et al., "Genetic Linkage Evidence for a Familial Alzheimer's Disease Locus on Chromosome 14", Science, 1992, 258:668–671.
Sherrington, R. et al., "Cloning a gene bearing missense mutations in early–onset familial Alzheimer's disease", Nature, 1995, 375:754–760.
St. George–Hyslop, P. et al., "Genetic evidence for a novel familial Alzheimer's disease locus on chromosome 14", Nature Genet., 1992, 2:330–334.
Van Broeckhoven, C. et al., "Mapping of a gene predisposing to early–onset Alzheimer's disease to chromosome 14q24.3", Nature Genet., 1992, 3:335–339.
Strom et al. A yeast GTPase–activating protein that interacts specifically with a member of the Ypt/Rab family. Nature 361:736–739 (Feb. 25, 1993).

*Primary Examiner*—Elizabeth Kemmerer
*Assistant Examiner*—David S. Romeo
*Attorney, Agent, or Firm*—William T. Han; Ratner & Prestia; William T. King

[57] ABSTRACT

This invention and relates to polynucleotide and polypeptide sequences of the Early Onset Alzheimer's Disease gene (herein "EOAD gene"). More particularly, this invention relates to fragments and mutants EOAD gene useful as probes and amplification primers for the identification of a predisposition or diagnosis of Alzheimer's Disease.

10 Claims, 8 Drawing Sheets

FIG. 1A

```
AGCTACGAGCCGCGGCAGCGGGCGGCGCGGGGAAGCACCTAATCTGGGAGCCTTTGCGGTCCTTAGACAGC
                                                                        90
TCGATGCTCGGCGCCGCTGCCGCCCCGCCCCCGCCGCGTCCTCGTGATTAGACCCTCGGAGTGTCACAACAGCCAGGAATCTGTCG
                                                                        180
TTGGCCTGGAGAGAACACATGAAAGAAAGAACCTCAAGAGGCTTTGTTTTCTGTGAAACAGTATTTCTATACAGTGCTCCAATGACAG
                                                                        270
AACCGGACCTCCTCTTGTGACTTTCTTCTTGGAGTTCTCCGAAACAAAAGACACTTTGTCATAAAGATATGTCAACGAGGTTACTGTC
                                                                  M  T
                                                                        270
AGTTACCTGCACCGTTGTCCTACTTCCAGAATGCACAGATGTCTGAGGACAACCACCTGAGCAATACTNNNNNNNNAATGACAATA

TCAATGACGTGGCAACAGGATGAAGGTCTTACGTGTCTACAGACTCCTGTTGGTGGACTCGTCGTTATGANNNNNNNNNTTACTGTTAT
     ↑
   VRSQ
   Splice
   Variant
 E  L  P  A  P  L  S  Y  F  Q  N  A  Q  M  S  E  D  N  H  L  S  N  T  X  X  X  X  N  D  N
                                                                        360
GAGAACGGCAGGAGCACAACGACAGACGGAGCCTTGGCCACCCTGAGCCATTATCTAAGTGACGACCCCAGGTAACTCCCGGCAGGTGG CTCTTGCCGTCCGTCCTCGTGTTGCTGTCGTCGAACCGGTGGGACTCGGTAATAGATTACCTGCTGGGGTCCATTGAGGGCCGTCCACC
 E  R  Q  E  H  N  D  R  R  S  L  G  H  P  E  P  L  S  N  G  R  P  Q  G  N  S  R  Q  V
                                                                        450
TGGAGCAAGATGAGGAAGAAGATGAGGAGCTGACATTGAAATGCGCCAAGCATGTGATCATGCTCTTTGTCCCTGTGACTCTCTGCA ACCTCGTTCTACTCCTTCTTCTACTCCTCGACTGTAACTTTATACGCGGTTCGTACACTAGTAGAAACAGGGACACTGAGAGACGT
 V  E  Q  D  E  E  E  D  E  E  L  T  L  K  Y  G  A  K  H  V  I  M  L  F  V  P  V  T  L  C
                                                                        540
TGGTGGTGGTCGTGGCTACCATTAAGTCAGTCAGTTTTATACCCGGAAGGATGGCAGCTAATCTATACCCCATTCACAGAAGATACCG ACCACCACCAGCACCGATGGTAATTCAGTCAGTCGAAATATGGGCCTTCCTACCCGTCGATTAGATATGGGGTAAGTGTCTTCTATGGC
```

FIG. 1B

```
     M   V   V   V   A   T   I   K   S   V   S   F   Y   T   R   K   D   G   Q   L   I   Y   T   P   F   T   E   D   T
   AGACTGTGGGGCCAGAGCCCTGCACTCAATTCTGAATGCTGCCATCATGATCAGTGTCATTGTTGTCATGACTATCCTCCTGGTGTTC
                                                                                              630
   TCTGACACCCGTCTCGGAGGTGAGTTAAGACTTACGACGTAGTACTAGTCACAGTAACAACAGTACTGATAGGAGGACCACCAAG

E   T   V   G   Q   R   A   L   H   S   I   L   N   A   A   I   M   I   S   V   I   V   V   M   T   I   L   L   V   V
   TGTATAAATACAGGTGCTATAAGGTCATCCATGCCTGGCTTATTATATCATCTCTATTGTTGCTGTGTTCTTTTTTTCATTCATTACTTGG
                                                                                              720
   ACATATTTATGTCCACGATATTCCAGTAGGTACGGACCGAATAATATAGTAGAGATAACAACGACAAGAAAAAAAGTAAGTAATGAACC

L   Y   K   Y   R   C   Y   K   V   I   H   A   W   L   I   I   S   S   L   L   L   F   F   F   S   F   I   Y   L
   GGGAAGTGTTTAAACCTATAACGTTGCTGTGGACTACATTACTGTTGCACTCCTGATCTGGAATTTTGGTGTGGTGGAATGATTTCCA
                                                                                              810
   CCCTTCACAAATTTGGATATTGCAACGACACCTGATGTAATGACAACGTGAGGACTAGACCTTAAACACCCTTACTAAAGGT

G   E   V   F   K   T   Y   N   V   A   V   D   Y   I   T   V   A   L   L   I   W   N   F   G   V   V   G   M   I   S
   TTTCACTGGAAAGTCCACTTCCAGCACTTCGACTTCAGCAGGCATATCTCATTATGATTAGTGCCCTGGTCCCTGGTGTTATCAAGTACTCCCTG
                                                                                              900
   AAGTGACCTTTCCAGGTGAAGCTGAAGTCGTCGAGTCGTCCGTATAGAGTAATACTAATCACGGGAGTACCGGGACACAAATAGTTCATGAGGGAC

I   H   W   K   G   P   L   R   L   Q   Q   A   Y   L   I   M   I   S   A   L   M   A   L   V   F   I   K   Y   L   P
   AATGGACTGCGTGGCTCATCTTGGCTGTGATTTCAGTATATATGATTAGTGGCTGCTGTTTTGTGTCCGAAAGGTCCACTTCGTATGCTGTGTTG
                                                                                              990
   TTACCTGACGCACCGAGTAGAACCGACACTAAAGTCATATACTAAATCACCGACGACAAAAAACAGGCTTTCCAGGTGAAGCATACGACCAAC

E   W   T   A   W   L   I   L   A   V   I   S   V   Y   D   L   V   A   V   L   C   P   K   G   P   L   R   M   L   V
   AAACAGCTCAGGAGAGAAATGAAACGCTTTTCCAGCTCCTCATTACTCCTCAACAATGGTGTGGTTGGTGAATATGGCAGAAGGAGACC
                                                                                              1080
   TTTGTCGAGTCCTCTCTTTACTTGCGAAAAGGTCGAGAGTAAATGAGGAGTTGTTACCACCAACCACTTATACCGTCTTCCTCTGG

```
CGGAAGCTCAAAGGAGAGTATCCAAAATTCCAAGTATAATGCAGAAAGCACAGAAAGGAGTCACAAGACACTGTTGCAGAGAATGATG
                                                                                      1170
GCCTTCGAGTTCCTCTCATAGGTTTTAAGGTTCATATTACGTCTCTTTGTGTCTTCTCCCTCAGTGTTCTCTGTGACAACGTCTCTTACTAC
 P  E  A  Q  R  R  V  S  K  N  S  K  Y  N  A  E  S  T  E  R  E  S  Q  D  T  V  A  E  N  D

ATGGCGGGTTCAGTGAGGAATGGGAAGCCCAGAGAGGACAGTCATCTAGGGCCTCATACCTGAGTCACGAGCTGCTGTCCAGG
                                                                                      1260
TACCGCCCAAGTCACTCCTTACCCTTCGGGTCTCTCCCTGTCAGTAGATCCCGGAGTAGCGACTCAGTGCTCGACGACAGGTCC
   G  G  F  S  E  E  W  E  A  Q  R  D  S  H  L  G  P  H  R  S  T  P  E  S  R  A  A  V  Q

AACTTTCCAGCAGTATCCTGCTGGTGAAGACCCAGTGGAGACTGGAACACAACCATAGCCTCTGTTCGTAGCCATATTAATTGGTTTGTGCCTTACATTAT
                                                                                      1350
TTGAAAGGTCGTCATAGGAGCGACCACTTCTGGGTCTCCTTCCCTCATTTGAACCTCTAAAGTAAAAGATGTCACAAGACC
 E  L  S  S  I  L  A  G  E  D  P  E  E  R  G  V  K  L  G  L  G  D  F  I  F  Y  S  V  L

TTGGTAAAGCCTCAGCAACAGCCAGTGAGACTGGAACACAACCATAGCCTCTGTTCGTAGCCATATTAATTGGTTTGTGCCTTACATTAT
                                                                                      1440
AACCATTTCGGAGTCGTTGTCGGTCACCTCTGACCTTGTGTTGGTATCGGACAAAGCATCGGTATAATTAACCAAACACGGAATGTAATA
 V  G  K  A  S  A  T  A  S  G  D  W  N  T  T  I  A  C  F  V  A  I  L  I  G  L  C  L  T  L

TACTCCTTGCCATTTCAAGAAAGTTCTTTCGTAAGGTCGAGAAGGTTAGAGGTAGTGGAAACCCGAACAAAAGATGAAACGGTGTCTAATAGAAC
                                                                                      1530
ATGAGGAACGGTAAAAGTTCTTTCAAGCATTGCCAGCTCTTCCAATCTCCAATCACCTTTGGGCTTGTTTTCTACTTTGCCACAGATTATCTTG
 L  L  A  I  F  K  K  A  L  P  A  L  P  I  S  I  T  F  G  L  V  F  Y  F  A  T  D  Y  L

TACAGCCTTTTATGGACCAATTAGCATTCCATCAATTTATATCTAGCATATTGCGGTTAGAATCCCAGGGATGTTTCTTNTTTGACTN
                                                                                      1620
ATGTCGGAAAATACCTGGTTAATCGTTAAGTAGTTAAAATATAGACGTATAAACGCCAATCTTAGGGTCCCTACAAAGAANAAACTGAN
 V  Q  P  F  M  D  Q  L  A  F  H  Q  F  Y  I  .
```

TAACAAATCTGGGGAGGACAAGGTGGTTNCCGTGTCNCCACATTNACAAGTCAAGNTCCCGTTGGACTTTGCAGTTCCTGCCAGTTTCCG
                                                                                    1710
ATTGTTTAGACCCCTCCTGTCCACCAAANGGCACANGGTGTAANTGTTCAGTTCNAGGGCAACCTGAAACGTCAAGGACGGTCAAAGGC

ACCANCTGCANTTTNGGACTTGGAGGGGNCCTAGGNAACGGTTTTGACCAA
                                      1762
TGGTNGACGTNAAANCCTGAACCTCCCCNGGATCCNTTGCCAAAACTGGTT

```
AGCTACGAGCCGCGCGGCGCAGCGGGGCGGGGAAGCACCTAATCTGGGAGCCTTTGCGGTCTTAGACAGC
       +         +         +         +         +         +         + 90
TCGATGCTCGGCGCGCCGCGTCGCCCCCGCCGCCCCTTCGTGATTAGACCCTCGGACGTTGTGCGAAACGCCAGGAATCTGTCG

TTGGCCTGAGGAGAACACATGAAAGAAGAAACCTCAAGAGGCTTTGTTTTCTGTGAAACAGTATTTCTATACAGTTGCTCCAATGACAG
       +         +         +         +         +         +         + 180
AACCGGACCTCCTCTTGTGTACTTTCTTCTTGGAGTTCTCCGAAACAAAAGACACTTTGTCATAAAGATATGTCAACGAGGTTACTGTC
                                                                     M   T

AGTTACCTGCACCGTTGTCCTACTTCCAGAATGCACAGATGTCTGAGGACAACCACCTGAGCAATACTAATGACAATAGAGAACGGCAGG
       +         +         +         +         +         +         + 270
TCAATGGACGTGGCAACAGGATGAAGGTCTTACGTGTCTACAGACTCCTGTTGGTGGACTCGTTATGATTACTGTTATCTCTTGCCGTCC

E   L   P   A   P   L   S   Y   F   Q   N   A   Q   M   S   E   D   N   H   L   S   N   T   N   D   N   R   E   R   Q
                                                                                                         ↑
                                                                                                       |VRSQ|
                                                                                                       |Splice|

AGCACACAACGACACAGACGGAGCCTTGGCCACCCTGAGCCATTATCTAATGACGACCCCAGGGTAACTCCCGGCCAGGTGGTGAGCAAGATG
       +         +         +         +         +         +         + 360
TCGTGTTGCTGTGTCTGCCTCGGAACCGGTGGGACTCGGTAATAGATTACTGCTGGGGTCCCATTGAGGGCCGGTCCACCACTCGTTCTAC

H   N   D   R   R   S   L   G   H   P   E   P   L   S   N   G   R   P   Q   G   N   S   R   Q   V   V   E   Q   D

AGGAAGAAGATGAGGAGCTGACATTGAAATATGGCGCCAAGCATGTGATCATGCTCTTTGTCCCTGTGACTCTCTGCATGGTGGTGGTCG
       +         +         +         +         +         +         + 450
TCCTTCTTCTACTCCTCGACTGTAACTTTATACCGCGGTTCGTACACTAGTAGCAGGAACAGGGACACTGAGAACGTACCACCACCAGC

E   E   D   E   E   L   T   L   K   Y   G   A   K   H   V   I   M   L   F   P   V   T   L   C   M   V   V   V

TGGCTACCATTAAGTCAGTCAGTCAGTTTATACCCGGAAGGATGGGCAGCTAATCTATACCCATTAGATATGGGTAAGTGTCTTCTATGGCC
       +         +         +         +         +         +         + 540
ACCGATGGTAATTCAGTCAGTCAGTCAAATATGGCCTTCCTACCCGTCGATTAGATATGGGGTAAGTGTCTTCATGAGGATACTGACACCCGG
```

FIG. 2B

```
     V   A   T   I   K   S   V   S   F   Y   T   R   K   D   G   Q   L   I   Y   T   P   F   T   E   D   T   E   T   V   G
     AGAGAGCCCTGCACTCAATTCTGAAATGCTGCCATCATGATCAGTGTCATTGTTGTCACTATCCTCCTGGTGTTCTGTATAAATACA
                                                                                              630
     TCTCTCGGGACTGAGTTAAGACTTTACGACGGTAGTACTAGTCACAGTAACACAGTAGGAGGACCACCAAGACATATTTATGT

Q   R   A   L   H   S   I   L   N   A   A   I   M   I   S   V   I   V   V   M   T   I   L   L   V   L   Y   K   Y
     GGTGCTATAAGGTCATCATCCATGCCCTGGCTTATTATATCATCTCTATTGTTGTGCTGTTCTTTTTTCATTTACTTGGGGAAGTGTTTA
                                                                                              720
     CACGATATTCCAGTAGTAGTACGGACCGAATAATAATAGTAGAGATAACAACAACGACAAGAAAAAAAGTAAATGAACCCCTTCACAAAT

R   C   Y   K   V   I   H   A   W   L   I   I   S   S   L   L   L   F   F   S   F   I   Y   L   G   E   V   F
     CACGATATTCCAGTAGTACGGACCGAATAATAGTAGAGATAACAACAACGACAAGAAAAAAAGTAAATGAACCCCTTCACAAAT
     AAACCTATAACGTTGCTGTGGACTACATTACTGTTGCACTCCTGATCTGGAATTTGTGTGGTGGGAATGATTCCATTCACTGAAAG
                                                                                              810
     TTTGGATATTGCAACGACACCTGATGTAATGACAACGTGAGGACTAGACCTTAAAACCACCCTTACTAAAGGTAAGTGACCTTTC

K   T   Y   N   V   A   V   D   Y   I   T   V   A   L   L   I   W   N   F   G   V   V   G   M   I   S   I   H   W   K
     GTCCACTTCGACTCCAGCAGGCATATCTCATTATGATTAGTGCCCTCGTGTGTTATCAAGTACCTCCCTGAATGGACTGCGT
                                                                                              900
     CAGGTGAAGCTGAGGTCGTCCGTATAGAGTAATACTAATCACCGGAGTACCGGGACCACAATAGTTCATGGAGGACTTACCTGACGCA

G   P   L   R   L   Q   Q   A   Y   L   I   M   I   S   A   L   M   A   L   V   F   I   K   Y   L   P   E   W   T   A
     GCTCTCATCTTGGCTGTGATTTCAGTATATATGATTAGTGCGTGTTTTGTGTCCGAAAGTCCACTTCGTATGCTGGTTGAAACAGCTCAGG
                                                                                              990
     CCGAGTAGAACCGACACTAAAGTCATATACTAATCACGACAAACAGAGGCTTTCCAGGTGAAGCATACGACCAACTTGTCGAGTCC

W   L   I   L   A   V   I   S   V   Y   D   L   V   A   V   L   C   P   K   G   P   L   R   M   L   V   E   T   A   Q
     AGAGAAATGAAACGCTTTTTCCAGCTCTCATTACTCCTCAACAATGGTGTGGTTGGTGAATATGGCAGAAGGAGACCCGGAAGCTCAGG
                                                                                              1080
     TCTCTTTACTTTGCGAAAAAGGTCGAGAGTAAATGAGGAGAGTTGTTACCACACCAACACTTATACCGTCTTCCTCTGGCCTTCGAGTTT

GGAGGACAAGGTGGTTNCCGTGTNCCACATTNACAAGTCAAGNTCCCGTTGGACTTTGCAGTTCCTGCCAGTTTCCGACCANCTGCANT 1710
CCTCCTGTTCCACCAAANGGCACANGGTGTAANTGTTCAGTTCNAGGGCAACCTGAAACGTCAAAGGACGGTCAAAGGCTGGTNGACGTNA

TTNGGACTTGGAGGGGNCCTAGGNAACGGTTTTGACCAA
AANCCTGAACCTCCCCNGATCCNTTGCCAAAACTGGTT 1750

FIG. 2D

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 1762 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

```
AGCTACGAGC CGCGGCGGCA GCGGGGCGGC GGGGAAGCAC CTAATCTGGG AGCCTGCAAG      60

TGACAACAGC CTTTGCGGTC CTTAGACAGC TTGGCCTGGA GGAGAACACA TGAAAGAAAG     120

AACCTCAAGA GGCTTTGTTT TCTGTGAAAC AGTATTTCTA TACAGTTCGT CCAATGACAG     180

AGTTACCTGC ACCGTTGTCC TACTTCCAGA ATGCACAGAT GTCTGAGGAC AACCACCTGA     240

GCAATACTNN NNNNNNNNNN AATGACAATA GAGAACGGCA GGAGCACAAC GACAGACGGA     300

GCCTTGGCCA CCCTGAGCCA TTATCTAATG GACGACCCCA GGGTAACTCC CGGCAGGTGG     360

TGGAGCAAGA TGAGGAAGAA GATGAGGAGC TGACATTGAA ATATGGCGCC AAGCATGTGA     420

TCATGCTCTT TGTCCCTGTG ACTCTCTGCA TGGTGGTGGT CGTGGCTACC ATTAAGTCAG     480

TCAGCTTTTA TACCCGGAAG GATGGGCAGC TAATCTATAC CCCATTCACA GAAGATACCG     540

AGACTGTGGG CCAGAGAGCC CTGCACTCAA TTCTGAATGC TGCCATCATG ATCAGTGTCA     600

TTGTTGTCAT GACTATCCTC CTGGTGGTTC TGTATAAATA CAGGTGCTAT AAGGTCATCC     660

ATGCCTGGCT TATTATATCA TCTCTATTGT TGCTGTTCTT TTTTTCATTC ATTTACTTGG     720

GGGAAGTGTT TAAAACCTAT AACGTTGCTG TGGACTACAT TACTGTTGCA CTCCTGATCT     780

GGAATTTTGG TGTGGTGGGA ATGATTTCCA TTCACTGGAA AGGTCCACTT CGACTCCAGC     840

AGGCATATCT CATTATGATT AGTGCCCTCA TGGCCCTGGT GTTTATCAAG TACCTCCCTG     900

AATGGACTGC GTGGCTCATC TTGGCTGTGA TTTCAGTATA TGATTAGTG GCTGTTTTGT     960

GTCCGAAAGG TCCACTTCGT ATGCTGGTTG AAACAGCTCA GGAGAGAAAT GAAACGCTTT    1020

TTCCAGCTCT CATTTACTCC TCAACAATGG TGTGGTTGGT GAATATGGCA GAAGGAGACC    1080

CGGAAGCTCA AAGGAGAGTA TCCAAAAATT CCAAGTATAA TGCAGAAAGC ACAGAAAGGG    1140

AGTCACAAGA CACTGTTGCA GAGAATGATG ATGGCGGGTT CAGTGAGGAA TGGGAAGCCC    1200

AGAGGGACAG TCATCTAGGG CCTCATCGCT CTACACCTGA GTCACGAGCT GCTGTCCAGG    1260

AACTTTCCAG CAGTATCCTC GCTGGTGAAG ACCCAGAGGA AAGGGGAGTA AAACTTGGAT    1320
```

```
TGGGAGATTT CATTTTCTAC AGTGTTCTGG TTGGTAAAGC CTCAGCAACA GCCAGTGGAG    1380

ACTGGAACAC AACCATAGCC TGTTTCGTAG CCATATTAAT TGGTTTGTGC CTTACATTAT    1440

TACTCCTTGC CATTTTCAAG AAAGCATTGC CAGCTCTTCC AATCTCCATC ACCTTTGGGC    1500

TTGTTTTCTA CTTTGCCACA GATTATCTTG TACAGCCTTT TATGGACCAA TTAGCATTCC    1560

ATCAATTTTA TATCTAGCAT ATTTGCGGTT AGAATCCCAG GGATGTTTCT TNTTTGACTN    1620

TAACAAATCT GGGGAGGACA AGGTGGTTTN CCGTGTNCCA CATTNACAAG TCAAGNTCCC    1680

GTTGGACTTT GCAGTTCCTG CCAGTTTCCG ACCANCTGCA NTTTNGGACT TGGAGGGGGN    1740

CCTAGGNAAC GGTTTTGACC AA                                             1762
```

(2) INFORMATION FOR SEQ ID NO:2:

(i) SEQUENCE CHARACTERISTICS:
        (A) LENGTH: 467 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Thr Glu Leu Pro Ala Pro Leu Ser Tyr Phe Gln Asn Ala Gln Met
 1               5                  10                  15

Ser Glu Asp Asn His Leu Ser Asn Thr Val Arg Ser Gln Asn Asp Asn
            20                  25                  30

Arg Glu Arg Gln Glu His Asn Asp Arg Arg Ser Leu Gly His Pro Glu
        35                  40                  45

Pro Leu Ser Asn Gly Arg Pro Gln Gly Asn Ser Arg Gln Val Val Glu
    50                  55                  60

Gln Asp Glu Glu Asp Glu Glu Leu Thr Leu Lys Tyr Gly Ala Lys
65                  70                  75                  80

His Val Ile Met Leu Phe Val Pro Val Thr Leu Cys Met Val Val Val
                85                  90                  95

Val Ala Thr Ile Lys Ser Val Ser Phe Tyr Thr Arg Lys Asp Gly Gln
            100                 105                 110

Leu Ile Tyr Thr Pro Phe Thr Glu Asp Thr Glu Thr Val Gly Gln Arg
        115                 120                 125

Ala Leu His Ser Ile Leu Asn Ala Ala Ile Met Ile Ser Val Ile Val
    130                 135                 140

Val Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175

Phe Ser Phe Ile Tyr Leu Gly Glu Val Phe Lys Thr Tyr Asn Val Ala
            180                 185                 190

Val Asp Tyr Ile Thr Val Ala Leu Leu Ile Trp Asn Phe Gly Val Val
        195                 200                 205

Gly Met Ile Ser Ile His Trp Lys Gly Pro Leu Arg Leu Gln Gln Ala
    210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255

Asp Leu Val Ala Val Leu Cys Pro Lys Gly Pro Leu Arg Met Leu Val
            260                 265                 270
```

```
Glu Thr Ala Gln Glu Arg Asn Glu Thr Leu Phe Pro Ala Leu Ile Tyr
            275                 280                 285
Ser Ser Thr Met Val Trp Leu Val Asn Met Ala Glu Gly Asp Pro Glu
        290                 295                 300
Ala Gln Arg Arg Val Ser Lys Asn Ser Lys Tyr Asn Ala Glu Ser Thr
305                 310                 315                 320
Glu Arg Glu Ser Gln Asp Thr Val Ala Glu Asn Asp Asp Gly Gly Phe
                325                 330                 335
Ser Glu Glu Trp Glu Ala Gln Arg Asp Ser His Leu Gly Pro His Arg
            340                 345                 350
Ser Thr Pro Glu Ser Arg Ala Ala Val Gln Glu Leu Ser Ser Ser Ile
        355                 360                 365
Leu Ala Gly Glu Asp Pro Glu Glu Arg Gly Val Lys Leu Gly Leu Gly
    370                 375                 380
Asp Phe Ile Phe Tyr Ser Val Leu Val Gly Lys Ala Ser Ala Thr Ala
385                 390                 395                 400
Ser Gly Asp Trp Asn Thr Thr Ile Ala Cys Phe Val Ala Ile Leu Ile
                405                 410                 415
Gly Leu Cys Leu Thr Leu Leu Leu Leu Ala Ile Phe Lys Lys Ala Leu
            420                 425                 430
Pro Ala Leu Pro Ile Ser Ile Thr Phe Gly Leu Val Phe Tyr Phe Ala
        435                 440                 445
Thr Asp Tyr Leu Val Gln Pro Phe Met Asp Gln Leu Ala Phe His Gln
    450                 455                 460
Phe Tyr Ile
465
```

(2) INFORMATION FOR SEQ ID NO:3:

(i) SEQUENCE CHARACTERISTICS:
        (A) LENGTH: 1750 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
AGCTACGAGC CGCGGCGGCA GCGGGGCGGC GGGGAAGCAC CTAATCTGGG AGCCTGCAAG    60

TGACAACAGC CTTTGCGGTC CTTAGACAGC TTGGCCTGGA GGAGAACACA TGAAAGAAAG   120

AACCTCAAGA GGCTTTGTTT TCTGTGAAAC AGTATTTCTA TACAGTTCGT CCAATGACAG   180

AGTTACCTGC ACCGTTGTCC TACTTCAGA ATGCACAGAT GTCTGAGGAC AACCACCTGA    240

GCAATACTAA TGACAATAGA GAACGGCAGG AGCACAACGA CAGACGGAGC CTTGGCCACC   300

CTGAGCCATT ATCTAATGGA CGACCCCAGG GTAACTCCCG GCAGGTGGTG GAGCAAGATG   360

AGGAAGAAGA TGAGGAGCTG ACATTGAAAT ATGGCGCCAA GCATGTGATC ATGCTCTTTG   420

TCCCTGTGAC TCTCTGCATG GTGGTGGTCG TGGCTACCAT TAAGTCAGTC AGCTTTTATA   480

CCCGGAAGGA TGGGCAGCTA ATCTATACCC CATTCACAGA AGATACCGAG ACTGTGGGCC   540

AGAGAGCCCT GCACTCAATT CTGAATGCTG CCATCATGAT CAGTGTCATT GTTGTCATGA   600

CTATCCTCCT GGTGGTTCTG TATAAATACA GGTGCTATAA GGTCATCCAT GCCTGGCTTA   660

TTATATCATC TCTATTGTTG CTGTTCTTTT TTTCATTCAT TTACTTGGGG GAAGTGTTTA   720

AAACCTATAA CGTTGCTGTG GACTACATTA CTGTTGCACT CCTGATCTGG AATTTTGGTG   780

TGGTGGGAAT GATTTCCATT CACTGGAAAG GTCCACTTCG ACTCCAGCAG GCATATCTCA   840
```

```
TTATGATTAG TGCCCTCATG GCCCTGGTGT TTATCAAGTA CCTCCCTGAA TGGACTGCGT      900

GGCTCATCTT GGCTGTGATT TCAGTATATG ATTTAGTGGC TGTTTTGTGT CCGAAAGGTC      960

CACTTCGTAT GCTGGTTGAA ACAGCTCAGG AGAGAAATGA AACGCTTTTT CCAGCTCTCA     1020

TTTACTCCTC AACAATGGTG TGGTTGGTGA ATATGGCAGA AGGAGACCCG GAAGCTCAAA     1080

GGAGAGTATC CAAAAATTCC AAGTATAATG CAGAAAGCAC AGAAAGGGAG TCACAAGACA     1140

CTGTTGCAGA GAATGATGAT GGCGGGTTCA GTGAGGAATG GGAAGCCCAG AGGGACAGTC     1200

ATCTAGGGCC TCATCGCTCT ACACCTGAGT CACGAGCTGC TGTCCAGGAA CTTTCCAGCA     1260

GTATCCTCGC TGGTGAAGAC CCAGAGGAAA GGGGAGTAAA ACTTGGATTG GGAGATTTCA     1320

TTTTCTACAG TGTTCTGGTT GGTAAAGCCT CAGCAACAGC CAGTGGAGAC TGGAACACAA     1380

CCATAGCCTG TTTCGTAGCC ATATTAATTG GTTTGTGCCT TACATTATTA CTCCTTGCCA     1440

TTTTCAAGAA AGCATTGCCA GCTCTTCCAA TCTCCATCAC CTTTGGGCTT GTTTTCTACT     1500

TTGCCACAGA TTATCTTGTA CAGCCTTTTA TGGACCAATT AGCATTCCAT CAATTTTATA     1560

TCTAGCATAT TTGCGGTTAG AATCCCAGGG ATGTTTCTTN TTTGACTNTA ACAAATCTGG     1620

GGAGGACAAG GTGGTTTNCC GTGTNCCACA TTNACAAGTC AAGNTCCCGT TGGACTTTGC     1680

AGTTCCTGCC AGTTTCCGAC CANCTGCANT TTNGGACTTG GAGGGGGNCC TAGGNAACGG     1740

TTTTGACCAA                                                           1750

(2) INFORMATION FOR SEQ ID NO:4:

(i) SEQUENCE CHARACTERISTICS:
        (A) LENGTH: 463 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Met Thr Glu Leu Pro Ala Pro Leu Ser Tyr Phe Gln Asn Ala Gln Met
  1               5                  10                  15

Ser Glu Asp Asn His Leu Ser Asn Thr Asn Asp Asn Arg Glu Arg Gln
                 20                  25                  30

Glu His Asn Asp Arg Arg Ser Leu Gly His Pro Glu Pro Leu Ser Asn
             35                  40                  45

Gly Arg Pro Gln Gly Asn Ser Arg Gln Val Val Glu Gln Asp Glu Glu
         50                  55                  60

Glu Asp Glu Glu Leu Thr Leu Lys Tyr Gly Ala Lys His Val Ile Met
 65                  70                  75                  80

Leu Phe Val Pro Val Thr Leu Cys Met Val Val Val Ala Thr Ile
                 85                  90                  95

Lys Ser Val Ser Phe Tyr Thr Arg Lys Asp Gly Gln Leu Ile Tyr Thr
                100                 105                 110

Pro Phe Thr Glu Asp Thr Glu Thr Val Gly Gln Arg Ala Leu His Ser
            115                 120                 125

Ile Leu Asn Ala Ala Ile Met Ile Ser Val Ile Val Val Met Thr Ile
        130                 135                 140

Leu Leu Val Val Leu Tyr Lys Tyr Arg Cys Tyr Lys Val Ile His Ala
145                 150                 155                 160

Trp Leu Ile Ile Ser Ser Leu Leu Leu Leu Phe Phe Phe Ser Phe Ile
                165                 170                 175

Tyr Leu Gly Glu Val Phe Lys Thr Tyr Asn Val Ala Val Asp Tyr Ile
```

-continued

```
                   180                 185                 190
    Thr Val Ala Leu Leu Ile Trp Asn Phe Gly Val Val Gly Met Ile Ser
                195                 200                 205

Ile His Trp Lys Gly Pro Leu Arg Leu Gln Gln Ala Tyr Leu Ile Met
            210                 215                 220

Ile Ser Ala Leu Met Ala Leu Val Phe Ile Lys Tyr Leu Pro Glu Trp
    225                 230                 235                 240

Thr Ala Trp Leu Ile Leu Ala Val Ile Ser Val Tyr Asp Leu Val Ala
                    245                 250                 255

Val Leu Cys Pro Lys Gly Pro Leu Arg Met Leu Val Glu Thr Ala Gln
                260                 265                 270

Glu Arg Asn Glu Thr Leu Phe Pro Ala Leu Ile Tyr Ser Ser Thr Met
            275                 280                 285

Val Trp Leu Val Asn Met Ala Glu Gly Asp Pro Glu Ala Gln Arg Arg
            290                 295                 300

Val Ser Lys Asn Ser Lys Tyr Asn Ala Glu Ser Thr Glu Arg Glu Ser
    305                 310                 315                 320

Gln Asp Thr Val Ala Glu Asn Asp Asp Gly Gly Phe Ser Glu Glu Trp
                    325                 330                 335

Glu Ala Gln Arg Asp Ser His Leu Gly Pro His Arg Ser Thr Pro Glu
                340                 345                 350

Ser Arg Ala Ala Val Gln Glu Leu Ser Ser Ser Ile Leu Ala Gly Glu
                355                 360                 365

Asp Pro Glu Glu Arg Gly Val Lys Leu Gly Leu Gly Asp Phe Ile Phe
            370                 375                 380

Tyr Ser Val Leu Val Gly Lys Ala Ser Ala Thr Ala Ser Gly Asp Trp
    385                 390                 395                 400

Asn Thr Thr Ile Ala Cys Phe Val Ala Ile Leu Ile Gly Leu Cys Leu
                    405                 410                 415

Thr Leu Leu Leu Leu Ala Ile Phe Lys Lys Ala Leu Pro Ala Leu Pro
                420                 425                 430

Ile Ser Ile Thr Phe Gly Leu Val Phe Tyr Phe Ala Thr Asp Tyr Leu
                435                 440                 445

Val Gln Pro Phe Met Asp Gln Leu Ala Phe His Gln Phe Tyr Ile
    450                 455                 460
```

EARLY ONSET ALZHEIMER'S DISEASE GENE AND GENE PRODUCTS

CROSS-REFERENCE TO RELATED APPLICATION

This application claims priority to U.S. Provisional Application Ser. No. 60/001,142 filed Jul. 13, 1995; and to U.S. Provisional Application Ser. No. 60/001,501 filed Jul. 18, 1995.

FIELD OF THE INVENTION

This invention relates to newly identified polynucleotides, polypeptides encoded by such polynucleotides, the use of such polynucleotides and polypeptides, as well as the production of such polynucleotides and polypeptides. More particularly, the polypeptides and polynucleotides of the present invention are the Early Onset Alzheimer's Disease (herein "EOAD") gene and splice variants of the gene, gene products and mutants and fragments thereof. The invention also relates to inhibiting the action of such polypeptides. More particularly, this invention relates to EOAD genes and segments of EOAD genes useful as probes and amplification primers for the identification of a predisposition for or diagnosis of Alzheimer's Disease. This invention also relates to full length genes and gene products useful for the treatment of neurodegenerative diseases, particularly Alzheimer's Disease.

BACKGROUND OF THE INVENTION

Alzheimer's disease (AD) is the fourth most common cause of death in the U.S. after heart disease, cancer and stroke. It presently afflicts more than four million people and this number is expected to double during the next forty years as the population ages. There is presently no cure for AD and treatments are largely palliative rather than treating the underlying causes of disease. A stated aim of the National Institute of Aging is to delay the age of onset by five years during the next five years and by ten years within the next ten years thus reducing significantly the number of people affected by AD.

Apart from advanced age and Down syndrome the only consistent risk factor for the development of AD identified in epidemiological surveys has been the presence of a positive family history of disease. The most striking evidence in support of genetic factors is the existence, amongst early onset cases of AD, of families in which the disease is inherited as a fully penetrant autosomal dominant disorder (Nee et al., Arch. Neurol. 40:203–208). The existence of large families with an inherited form of AD has enabled a genetic linkage strategy to be used to localize the disease genes.

The observation of AD neuropathology in aging Down syndrome (DS) patients led researchers to analyze chromosome 21 in families with an inherited form of AD. Genetic linkage between FAD and markers on the long arm of chromosome 21 was first reported in 1987 (St. George-Hyslop, et al., Nature, 347:194–197. (1990)). Since that time it has been demonstrated that early onset FAD is genetically heterogeneous and that many pedigrees do not show linkage to chromosome 21 markers (St. George-Hyslop, et al., Nature Genetics, 2:330–334 (1992) and Schellenberg, et al., Annals Of Neurology 31:223–227 (1992)).

Genetic linkage studies have identified a second locus causing early onset FAD (herein "early onset Alzheimers Disease" or "EOAD") on the long arm of chromosome 14 (Schellenberg, et al., Annals Of Neurology 31:223–227 (1992); Van Broeckhoven, et al., Nature Genetics 2:335–339 (1992); St. George-Hyslop, et al., Nature Genetics, 2:330–334 (1992)) linkage was first reported to D14S43 and localized to a region of about 23cM between D14S52 and D14SS3. The isolation of additional genetic markers has led to the candidate region being narrowed to a distance of 6.4 cM between D14S289 and D14S61 (Cruts, et al., Human Molecular Genetics. A positional cloning strategy is presently being used in our tab and others to identify the defective gene. Although the majority of EOAD families studied show linkage to this locus, at least one more locus causing early onset FAD must exist because the Volga German families show recombination with the APP gene and the markers tightly linked to the FAD gene on chromosome 14 (Schellenberg, et al., Science 25:668–671(1992). Apart from age of onset of disease no phenotypic or neuropathological markers have been identified that distinguish between the different causes of FAD. Identification of new chromosome 14-linked families for meiotic mapping and the successful application of linkage disequilibrium techniques (both of which could narrow down the region of interest considerably) could be key factors in the rapid identification of this gene since 6.4 cM of DNA could contain hundreds of candidate genes.

When the AD3 locus was first localized to chromosome 14 two genes were known to map to this region of the chromosome: the heat shock protein, HSPA2 and the protooncogene cfos. Refinement in the mapping of HSPA2 and the identification of additional recombinants in AD families now place the HSPA2 gene outside the candidate region cfos remains within the candidate region. However, extensive sequencing of the coding region by several groups has failed to reveal any pathogenic mutations although several polymorphisms have been identified and physical characterization of the early onset Alzheimer's disease AD3 locus on chromosome 14q24.3. Two expressed sequence tagged sites (ESTs) have also been mapped just outside the candidate region: D14S1O 2E, which maps between D14S289 and D14S251 and D14S1O1E, which maps between D14S61 and D14S59. Two other genes and one pseudogene have been mapped within the candidate region. The known genes are transforming growth factor beta (tgf-β), and the Kreb's cycle enzyme dihydrolipoamide succinyltransferase (DLST). Since tgf-β is known to modulate APP expression it represents a plausible candidate gene. To date no mutations have been identified in this gene in patients from chromosome 14-linked FAD cases. A reduction in the activity of DLST has been reported in brains from AD cases and also in the fibroblasts from chromosome 14-linked AD cases. However, to date no mutations have been identified in this gene in patients from chromosome 14-linked FAD cases.

The amino acid sequence of a non-splice form of the EOAD protein was recently diclosed (Sherrington, Nature 375:754 (1995)). Neither the splice variant of the EOAD gene nor the full length gene sequence of the EOAD were disclosed.

There is a clear need for treatments for this disease and the present invention relates to compounds and methods of treatment. Moreover, identification of such EOAD has been hampered by the unavailability of convenient diagnostic materials and methods. Thus, there is also a need for a rapid, sensitive, and specific test to aid in the diagnosis of EOAD. DNA-based diagnostic tests not only are sensitive and specific but also have the advantage of being rapid. Early detection and identification of EOAD facilitate prompt, appropriate treatment and care. The invention includes embodiments which are DNA sequences that are unique to the EOAD gene and comprise nucleic acid mutations are useful as diagnostic probes to detect the EOAD or a predisposition for EOAD.

This invention provides a unique novel set of DNA sequences useful for the detection of EOAD gene mutations, and particularly useful as primers and probes for the detection of EOAD or a predisposition for EOAD.

BRIEF DESCRIPTION OF THE INVENTION

In one aspect, the present invention is directed to each of the DNA sequences and molecules (and corresponding RNA sequences) identified in FIGS. 1A, 1B, 1C, 1D, 2A, 2B, 2C, and 2D (SEQ ID NO:1) and (SEQ ID NO:3) and to fragments or portions of such sequences which contain at least 15 bases, and preferably at least 50 bases, and to those sequences which are at least 95% and preferably at least 97% identical thereto, and to DNA (RNA) sequences encoding the same polypeptide as the sequences of FIGS. 1A, 1B, 1C, 1D, 2A, 2B, 2C, and 2D (SEQ ID NO:2) and (SEQ ID NO:4) as well as fragments and portions thereof.

In addition, the present invention relates to fragments or portions of the isolated DNA sequences of FIGS. 1A, 1B, 1C, 1D, 2A, 2B, 2C, and 2D (SEQ ID NO:1) and (SEQ ID NO:3) (and corresponding RNA sequences) containing at least 15 bases, preferably at least 40 bases and more preferably at least 50 bases, as well as sequences which are at least 97% identical thereto, as well as DNA (RNA) sequences encoding the same polypeptide.

As used herein, a first DNA (RNA) sequences is at least 95% and preferably at least 97% identical to another DNA (RNA) sequence if there is at least 95% and preferably at least a 95% or 97% identity, respectively, between the bases of the first sequence and the bases of the other sequence, when properly aligned with each other, for example when aligned by BLAST or FAST A.

In yet another aspect, the present invention is directed to an isolated DNA (RNA) sequence or molecule comprising at least the coding region of a human gene (or a DNA sequence encoding the same polypeptide as such coding region), in particular an expressed human gene, which human gene comprises a DNA sequence listed in FIGS. 1A, 1B, 1C, 1D, 2A, 2B, 2C, and 2D (SEQ ID NO:1) and (SEQ ID NO:3) or one at least 95% and preferably at least 97% identical thereto, as well as fragments or portions of the coding region which encode a polypeptide having a similar function to the polypeptide encoded by the coding region. Thus, the isolated DNA (RNA) sequence can include only the coding region of the expressed gene (or fragment or portion thereof as hereinabove indicated) or can further include all or a portion of the non-coding DNA of the expressed human gene.

In yet another aspect, the present invention is directed to an isolated DNA sequence (RNA) containing at least the coding region of a human gene of a DNA (RNA) sequence encoding the same peptide as such coding region (in particular, an expressed human gene) which human gene (either in the coding or non-coding region and in general, in the coding region) contains a DNA sequence identical to a DNA sequence present in FIGS. 1A, 1B, 1C, 1D, 2A, 2B, 2C, and 2D (SEQ ID NO:1) and (SEQ ID NO:3). The invention further relates to fragments or portions of such coding region which encode a polypeptide having a similar function to the polypeptide encoded by the coding region.

The present invention further relates to polypeptides encoded by such hereinabove noted DNA (RNA sequences, as well as the production and use of such polypeptides and fragments, derivatives and structural modifications thereof with the same function(s) and use(s) and to antibodies against such polypeptides.

The present invention also relates to vectors or plasmids which include such DNA (RNA) sequences, as well as the use of the DNA (RNA) sequences.

The sequences of a full length EOAD gene and splice variant is illustrated in FIGS. 1A, 1B, 1C, 1D, 2A, 2B, 2C, and 2D (SEQ ID NO:1) and (SEQ ID NO:3) respectively. FIGS. 1A, 1B, 1C, 1D, 2A, 2B, 2C, and 2D (SEQ ID NO:1) and (SEQ ID NO:3) do comprise the whole coding region for an EOAD gene; FIG. 2 (SEQ ID NO:3) is a splice variant.

Various aspects of the present invention thus include each of the partial and complete EOAD cDNA, mRNA, antisense strands, triple helix probes, PCR primers, coding regions, and constructs. Expression vectors and polypeptide expression products, are also within the scope of the present invention, along with antibodies, especially monoclonal antibodies, to such expression products.

This invention relates to an isolated polypeptide sequences having the sequence selected from the group of amino acid sequences given herein as FIGS. 1A, 1B, 1C, 1D, (SEQ ID NO:2) and (SEQ ID NO:4) 2A, 2B, 2C, and 2D.

This invention further relates to a gene comprising the sequence selected from the group of sequences depicted in FIGS. 1A, 1B, 1C, and 1D (SEQ ID NO:1) or (SEQ ID NO:3) FIGS. 2A, 2B, 2C, and 2D.

In another aspect, the invention relates to an isolated DNA sequence comprising DNA having at least a 95% identity to a DNA sequence selected from FIGS. 1A, 1B, 1C, and 1D (SEQ ID NO:1) or FIGS. 2A, 2B, 2C, and 2D (SEQ ID NO:3).

In yet another aspect, the invention relates to an isolated sequence comprising RNA corresponding to any of the DNA sequences or fragments of FIGS. 1A, 1B, 1C, and 1D (SEQ ID NO:1) or FIGS. 2A, 2B, 2C, and 2D (SEQ ID NO:3).

In yet a further aspect, the invention relates to an isolated polynucleotide having the sequence set forth in FIG. 1A, 1B, 1C, and 1D (SEQ ID NO:1) or FIGS. 2A, 2B, 2C, and 2D (SEQ ID NO:3), which is the EOAD gene and EOAD gene splice variant respectively which encodes the EOAD gene product and EOAD splice variant gene product respectively.

In accordance with one aspect of the present invention, there is provided a novel mature polypeptide which is the EOAD gene product, as well as fragments, analogs and derivatives thereof. The polypeptide of the present invention is of human origin.

In accordance with one aspect of the present invention, there is provided a polynucleotide encoding the same mature polypeptide as a human gene whose coding region includes a nucleotide sequence selected from the group consisting of the nucleotide sequences of FIGS. 1A, 1B, 1C, and 1D (SEQ ID NO:1) and FIGS. 2A, 2B, 2C, and 2D (SEQ ID NO:3).

In accordance with another aspect of the present invention, there are provided polynucleotides (DNA or RNA) which encode such polypeptides.

In accordance with yet a further aspect of the present invention, there is provided a process for producing such polypeptide by recombinant techniques.

In accordance with yet a further aspect of the present invention, there is provided a process for utilizing such polypeptide, or polynucleotide encoding such polypeptide for therapeutic purposes, for example, for the treatment of Alzheimer's Disease, particularly EOAD.

In accordance with yet a further aspect of the present invention, there is provided an antibody against such polypeptides.

In accordance with yet another aspect of the present invention, there are provided antagonist/inhibitors to such polypeptides, which may be used to inhibit the action of such polypeptides, for example, in the treatment of Alzheimer's Disease, especially for the treatment of EOAD.

These and other aspects of the present invention should be apparent to those skilled in the art from the teachings herein.

The following drawings are illustrative of embodiments of the invention and are not meant to limit the scope of the invention as encompassed by the claims.

BRIEF DESCRIPTION OF THE FIGURES

FIG. 1A, 1B, 1C, and 1D illustrates the full length cDNA and the amino acid sequence of the EOAD gene sequence (SEQ ID NOS:1 and 2, respectively).

FIG. 2A, 2B, 2C, and 2D illustrates the full length cDNA and the amino acid sequence of the EOAD splice variant gene sequence (SEQ ID NOS:3 and 4, respectively).

DETAILED DESCRIPTION OF THE INVENTION

Nucleic acid-based methods for the detection of human diseases or a predisposition for human disease using clinical samples can be separated into two broad categories, differing primarily in the lower limit of detection of the target nucleic acid sequence. The first category employs conventional molecular techniques to detect target sequences directly from clinical samples. The second category, predicated on nucleic acid amplification technologies, rapidly enriches the target sequences prior to detection. The determination of which approach to employ depends on a number of factors such as cost, labor and the clinical need for rapid results. The nucleic acid molecules of this invention may be advantageously and simply employed in either of the two systems.

Conventional methods for nucleic acid detection rely on physico-chemical methods to foster visualization the molecules or rely on hybridization methodology employing nucleic acid probes which are labeled with analytically detectable reagents. Examples include: Southern blotting whereby endonuclease-digested DNA is immobilized on supports such as nitrocellulose filters then probed with analytically labeled nucleic acid to detect specific complementary sequences. Analytically detectable reagents for this purposes include radioactive isotopes (e.g., $^{14}C$ and $^{32}P$) and non-radioactive reagents such as chemiluminescent materials, DNA dot blots whereby DNA is extracted from a number of clinical isolates by any convenient means and transferred by numerous methods known in the art, including but not limited to vacuum filtration, to a support and probed as is the case of Southern blotting; and Colony dot blots whereby the colonies comprising human gDNA or cDNA derived from clinical isolates are cultured on agar plates, transferred to paper and lysed in situ prior to probing.

Amplification systems rely on the existence of primer nucleic acid molecules of about 10–30 nucleotides in length which flank the target region. The primer acts as initiation points for multiple cycles of DNA replication on the region defined by the flanking primers. The Polymerase Chain Reaction (PCR) employing the Taq DNA polymerase (Mullis et al., Meth. Enzymol. 155:335–350(1987)) is a classic example of an amplification system.

Figure 2C:
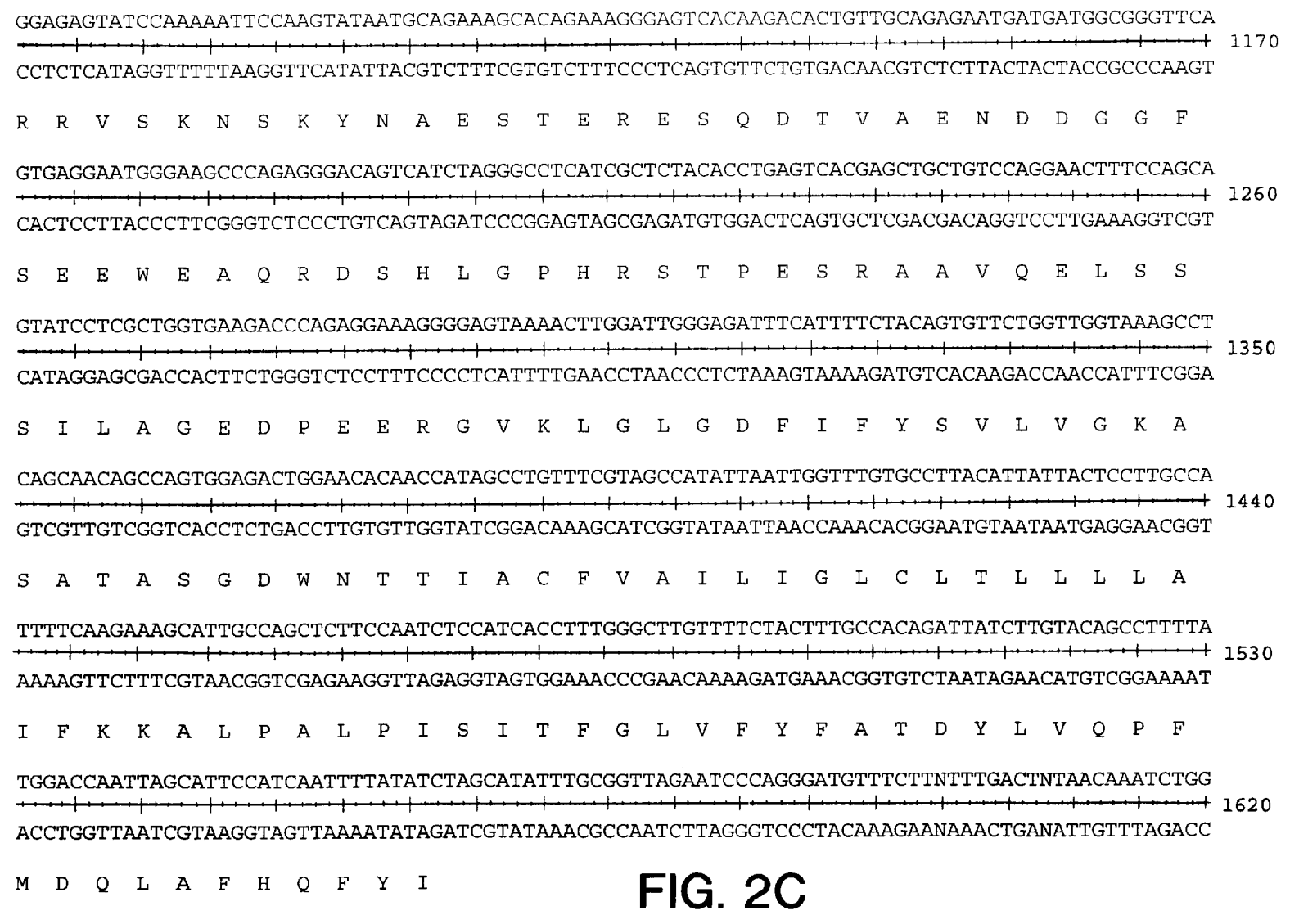

In the invention the nucleotide indicated by the letter N in FIGS. 1A, 1B, 1C, and 1D (SEQ ID NO:1) and FIGS. 2A, 2B, 2C, and 2D (SEQ ID NO:3) can be selected from the group consisting of A, C, G and T.

Recombinant Production Techniques and Purification

"Substantially equivalent," can refer both to nucleic acid and amino acid sequences, for example a mutant sequence, that vary from a reference sequence by one or more substitutions, deletions, or additions, the net effect of which does not result in an adverse functional dissimilarity between reference and subject sequences. For purposes of the present invention, sequences having equivalent biological activity, and equivalent expression characteristics are considered substantially equivalent. For purposes of determining equivalence, truncation of the mature sequences should be disregarded.

In accordance with an aspect of the present invention, there is provided an isolated nucleic acid (polynucleotide) which encodes for the mature polypeptide comprising a polypeptide fragment selected from the group consisting of polypeptides depicted in FIGS. 1A, 1B, 1C, and 1D (SEQ ID NO:2) and FIGS. 2A, 2B, 2C, and 2D (SEQ ID NO:4).

The polynucleotides of the present invention may be in the form of RNA or in the form of DNA, which DNA includes cDNA, genomic DNA (gDNA), and synthetic DNA. The DNA may be double-stranded or single-stranded, and if single stranded may be the coding strand or non-coding (anti-sense) strand. The coding sequence which encodes the mature polypeptide may be identical to the coding sequence shown in FIGS. 1A, 1b, 1C, and 1D (SEQ ID NO:1) or FIGS. 2A, 2B, 2C, and 2D (SEQ ID NO:3) or may be a different coding sequence which coding sequence, as a result of the redundancy or degeneracy of the genetic code, encodes the same, mature polypeptide as the wild-type DNA comprising the DNA sequence of FIGS. 1A, 1B, 1C, and 1D (SEQ ID NO:1) or FIGS. 2A, 2B, 2C, and 2D (SEQ ID NO:3).

The polynucleotide comprising a sequence of FIG. 1 (SEQ ID NO:1) or 2 (SEQ ID NO:3) which encodes the mature polypeptide may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide comprising a deduced amino acid sequence of FIG. 1A, 1B, 1C, and 1D (SEQ ID NO:2) or FIGS. 2A, 2B, 2C, and 2D (SEQ ID NO:4). The variant of the polynucleotide may be a naturally occurring allelic variant of the polynucleotide or a non-naturally occurring variant of the polynucleotide.

Thus, the present invention includes polynucleotides encoding the same mature polypeptide comprising a polypeptide as shown in FIGS. 1A, 1B, 1C, and 1D (SEQ ID NO:2) or FIGS. 2A, 2B, 2C, and 2D (SEQ ID NO:4) of such polynucleotides which variants encode for a fragment, derivative or analog of the polypeptide comprising a polypeptide of FIGS. 1A, 1B, 1C, and 1D (SEQ ID NO:2) or FIGS. 2A, 2B, 2C, and 2D (SEQ ID NO:4). Such nucleotide variants include deletion variants, substitution variants and addition or insertion variants.

As hereinabove indicated, the polynucleotide may have a coding sequence which is a naturally occurring allelic variant of the gene comprising a polynucleotide coding sequence shown in FIGS. 1A, 1B, 1C, and 1D (SEQ ID NO:1) or FIGS. 2A, 2B, 2C, and 2D (SEQ ID NO:3). As known in the art, an allelic variant is an alternate form of a polynucleotide sequence which may have a substitution, deletion or addition of one or more nucleotides, which does not substantially alter the function of the encoded polypeptide.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, et al., *Cell*, 37:767 (1984)).

The present invention further relates to polynucleotides which hybridize to the hereinabove-described sequences if there is at least 50% and preferably 70% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which retain substantially the same biological function or activity as the mature polypeptide encoded the gene comprising a polynucleotide of FIGS. 1A, 1B, 1C, and 1D (SEQ ID NO:1) or FIGS. 2A, 2B, 2C, and 2D (SEQ ID NO:3).

The terms "fragment," "derivative" and "analog" when referring to the a polypeptide or gene product comprising the sequence of the polypeptide of FIGS. 1A, 1B, 1C, and 1D (SEQ ID NO:2) or FIGS. 2A, 2B, 2C, and 2D (SEQ ID NO:4) or that encoded by the clone in the deposited cDNA library, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of comprising a sequence of FIGS. 1A, 1B, 1C, and 1D (SEQ ID NO:2) or 2A, 2B, 2C, and 2D (SEQ ID NO:4) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the EOAD genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Salmonella typhimurium; fungal cells, such as yeast; insect cells such as Drosophila and Sf9; animal cells such as CHO, COS or Bowes melanoma; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pbs, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. (Davis, et al., *Basic Methods in Molecular Biology*, (1986)).

The constructs in host cells can be used in a conventional manner to produce the gene product encoded by the recombinant sequence. Alternatively, the polypeptides of the invention can be synthetically produced by conventional peptide synthesizers.

Mature proteins comprising the amino acid sequence in FIG. 1 (SEQ ID NO:2) and 2 (SEQ ID NO:4) can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., *Molecular Cloning: A Laboratory Manual*, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a -downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, *Cell*, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptides of the invention can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography hydroxylapatite chromatography and lectin chromatography. It is preferred to have low concentrations (approximately 0.15–5 mM) of calcium ion present during purification. (Price et al., *J. Biol. Chem.*, 244:917 (1969)). Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

While the specification complies with the requirements of 35 USC §112 without a deposit of any biological material, solely for the convenience and benefit of the public, a full length cDNA clone of S182 from a human brain library was deposited with ATCC as Deposit Number 97238 (pcDNA+ S182 clone 1b) on Jul. 28, 1995 in compliance with Budapest Treaty. This clone will be made available irrevocably and without restriction, expect as conditioned by CFR 1.808(b), upon issuance of a patent. The depository address is the American Type Culture Collection, 12301 Parklawn Drive, Rockville, Md. 20852, USA.

Kits, Therapeutic Methods and Compositions

The polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

The polypeptides of the present invention may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

The pharmaceutical compositions may be administered in a convenient manner such as by the oral, topical, intravenous, intraperitoneal, intramuscular, subcutaneous, intranasal or intradermal routes. The amounts and dosage regimens of EOAD polypeptides of the invention administered to a subject will depend on a number of factors such as the mode of administration, the nature of the condition being treated and the judgment of the prescribing physician. Generally speaking, they are given, for example, in therapeutically effective doses of at least about 10 mg/kg body weight. Preferably the dosage is from about 10 mg/kg to about 1 mg/kg body weight daily, taking into account the routes of administration, symptoms, etc.

The present invention is further directed to inhibiting Alzheimer's Disease, preferably EOAD, in vivo by the use of antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.*, 6:3073 (1979); Cooney et al, *Science*, 241:456 (1988); and Dervan et al., *Science*, 251: 1360 (1991)), thereby preventing transcription and the production of mutant EOAD gene products. The antisense RNA oligonucleotide hybridizes to the mRNA in vivo and blocks translation of the mRNA molecule into the MCP-4 (antisense—Okano, J. *Neurochem.*, 56:560 (1991); Oligodeoxynucleotides as Antisense Inhibitors of Gene Expression, CRC Press, Boca Raton, Fla. (1988)).

Alternatively, the oligonucleotides described above can be delivered to cells by procedures in the art such that the antisense RNA or DNA may be expressed in vivo to inhibit production of mutant EOAD gene products in the manner described above.

Accordingly, antisense constructs to the EOAD polypeptide can be used to treat EOAD.

The present invention is also directed to antagonist/inhibitors of the mature polypeptides comprising the polypeptide sequences of the present invention. The antagonist/inhibitors are those which inhibit or eliminate the function of the mature polypeptide.

Thus, for example, antagonists bind to a mature polypeptide of the present invention and inhibit or eliminate its function. The antagonist, for example, could be an antibody against the polypeptide which binds to the polypeptide or, in some cases, an oligonucleotide. An example of an inhibitor is a small molecule which binds to and occupies the catalytic or binding site of the mature polypeptide thereby making the catalytic or binding site inaccessible to substrate or ligand such that normal biological activity is prevented. Examples of small molecules include but are not limited to small peptides or peptide-like molecules.

Alternatively, antagonists to the genes and polypeptides comprising a polypeptide of the present invention may be employed which bind to the receptors to which a polypeptide of the present invention normally binds. The antagonists may be closely related proteins such that they recognize and bind to the receptor sites of the natural protein, however, they are inactive forms of the polypeptide and thereby prevent the action of the EOAD polypeptide since receptor sites are occupied. In these ways, the antagonist/inhibitors may be used to treat Alzheimer's Disease, preferably EOAD.

The antagonist/inhibitors may be employed in a composition with a pharmaceutically acceptable carrier, e.g., as hereinabove described.

The present invention will be further described with reference to the following examples; however, it is to be understood that the present invention is not limited to such examples. All parts or amounts, unless otherwise specified, are by weight.

EOAD Primers, Probes and Methods of Use

The present invention advantageously provides both probes and primers which detect a variety of mutant EOAD genes. Probes of the invention are useful as an initial screen for EOAD or a predisposition for EOAD, and provide a rapid alternative to traditional behavioral diagnosis of EOAD using observation and analysis of patient behavior which may lead to misdiagnosis through confusion with other dementias.

Nucleotide sequences are presented herein by single- and double-strand in the 5' to 3' direction, from left to right. The skilled artisan can use double- and single-stranded probes for hybridization analyses using methods of the invention as as for other methods known in the art. One letter nucleotide symbols, A,C, G and T, used herein have their standard meaning in the art in accordance with the recommendations of the IUPAC-IUB Biochemical Nomenclature Commission and the Patent Office Rules. Nucleotide symbol N disclosed herein can stand for any of the nucleotides A, C, G or T. All of the finite variations of the sequences herein are embodiments of the invention and are useful in the methods of the invention. Herein "complement" refers to sequence which is "complementary" as that term is used in the art.

The term "amplification pair," as used herein, refers to a pair of oligonucleotide probes of the present invention selected to be suitable for use together in amplifying a selected EOAD gene nucleic acid sequence by a process such as polymerase chain reaction, ligase chain reaction, or strand displacement amplification, as explained in greater detail below.

Nucleic acid (i.e., DNA, gDNA, cDNA or RNA) samples for practicing the present invention may be obtained from any suitable source. Typically, the nucleic acid sample will be obtained in the form of a sample of a biological fluid or biological tissue suspected of containing a mutant EOAD gene and/or from a patient suspected of having EOAD or a predisposition for EOAD. Suitable biological fluids include, but are not limited to, blood, lymph, cerebrospinal fluid and saliva. Suitable tissue samples include, but are not limited to, skin and soft tissue samples such as neural tissue and brain tissue.

Oligonucleotide primers and probes of the present invention may be derived from the sequences of the present invention, being fragments of such sequences and being of any suitable length, depending on the particular assay format employed. In general, the oligonucleotide primers are at least about 10 to about 30 nucleotides in length. For example, oligonucleotide primers used for detecting EOAD are preferably 15 to 20 nucleotides in length. The oligonucleotide probes may incorporate the elements of a strand displacement amplification pairs of oligonucleotide probes are directed are preferably 50 to 150 nucleotides in length. Fro the sequences disclosed, the skilled artisan can readily determine what length fragments to use for the particular analysis employed considering, for example, the nucleic acid content of the fragment.

With respect to nucleic acid sequences which hybridize to specific nucleic acid sequences disclosed herein, hybridization may be carried out under conditions of reduced stringency, medium stringency or even stringent conditions (e.g., conditions represented by a wash stringency of 0.5× SSC and 0.1% SDS at a temperature of 20 or 30 degrees below the melting temperature of the probe, or even conditions represented by a wash stringency of 0.1×SSC and 0.1% SDS at a temperature of 10 degrees below the melting temperature of the DNA sequence to target DNA) in a standard hybridization assay. See J. Sambrook et al., *Molecular Cloning, A Laboratory Manual* (2d Ed. 1989) (Cold Spring Harbor Laboratory). In general, nucleic acid sequences which hybridize to the DNA disclosed herein will have at least 65% sequence similarity, 70% sequence similarity and even 75% or greater sequence similarity with the sequence of DNA disclosed herein.

Probes of the invention can be utilized with naturally occurring sugar-phosphate backbones as well as modified backbones including phosphorothioates, dithionates, alkyl phosphonates and α-nucleotides. Modified sugar-phosphate backbones are generally illustrated by Miller and T'so, *Ann. Reports Med. Chem.*, 23:295 (1988) and Moran et al., *Nuc. Acids Res.*, 14:5019 (1987). Probes of the invention can be constructed of either ribonucleic acid (RNA) or deoxyribonucleic acid (DNA), with DNA preferred.

Use of the probes in detection methods include Northern blots (RNA detection), Southern blots (DNA detection), western blots (protein detection), and dot blots (DNA, RNA or protein),as discussed above. Other detection methods include kits containing probes on a dipstick setup and the like.

To detect hybrid molecules formed from using the probes of the invention, typically an analytically detectable marker is added to one of the probes. Probes can be labeled by several methods. Probes can be radiolabelled and detected by autoradiography. Such labels for autoradiography include $^3$H, $^{125}$I, $^{35}$S, $^{14}$C, and $^{32}$P. Typically the choice of radioactive isotopes depends on research preferences involving ease of synthesis, stability, and half lives of the isotopes. Other detectable markers include ligands, fluorophores chemiluminescent agents, electrochemical via sensors, time-resolved fluorescence, enzymes, and antibodies. For example, an antibody can be labeled with a ligand. Other detectable markers for use with probes of the invention include biotin, radionucleotides, enzyme inhibitors, co-enzymes, luciferins, paramagnetic metals, spin labels, and monoclonal antibodies. The choice of label dictates the manner in which the label is bound to the probe.

Radioactive nucleotides can be incorporated into probes of the invention by several means. Such means include nick translation of double-stranded probes, copying single-stranded M13 plasmids having specific inserts with the Klenow fragment of DNA polymerase I of *E. coli* or other such DNA polymerase in the presence of radioactive dNTP, transcribing cDNA from RNA templates using reverse transcriptase in the presence of radioactive dNTP, transcribing RNA from vectors containing strong promoters such as SP6 promoters or T7 promoters using SP6 or T7 RNA polymerase in the presence of radioactive rNTP, tailing the 3' ends of probes with radioactive nucleotides using terminal transferase, and by phosphorylation of the 5' ends of probes using gamma $^{32}$P ATP and polynucleotide kinase.

Amplification of a selected, or target, nucleic acid sequence may be carried out by any suitable means. See generally, D. Kwoh and T. Kwoh, *Am. Biotechnol. Lab.* 8: 14–25(1990). Examples of suitable amplification techniques include, but are not limited to, polymerase chain reaction, ligase chain reaction, strand displacement amplification, transcription-based amplification (See: D. Kwoh et al., *Proc. Nat'l. Acad. Sci. USA* 86:1173–1177 (1989)), self-sustained sequence replication (See: J. Guatelli et al., *Proc. Natl. Acad. Sci. USA* 87:1874–1878 (1990)), and the Qβ replicase system (See: P. Lizardi et al., *BioTechnology* 6:1197–1202 (1988)).

Polymerase chain reaction (PCR) is carried out in accordance with known techniques. See, e.g.,: U.S. Pat. Nos. 4,683,195; 4,683,202; 4,800,159; and 4,965,188 (the disclosure of all U.S. Patent references cited herein are to be incorporated herein by reference). In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized which is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps are cyclically repeated until the desired degree of amplification is obtained. Detection of the amplified sequence may be carried out by adding to the reaction product an oligonucleotide probe capable of hybridizing to the reaction product (e.g., an oligonucleotide probe of the present invention), the probe carrying a detectable label, and then detecting the label in accordance with known techniques.

Ligase chain reaction (LCR) is carried out in accordance with known techniques. See, e.g., R. Weiss, *Science* 254:1292 (1991). In general, the reaction is carried out with two pairs of oligonucleotide probes; one pair binds to one strand of the sequence to be detected; the other pair binds to the other strand of the sequence to be detected. Each pair together completely overlaps the strand to which it corresponds. The reaction is carried out by, first denaturing (e.g., separating) the strands of sequence to be detected, then reacting the strands with the two pairs of oligonucleotide probes in the presence of a heat stable ligase so that each pair of oligonucleotide probes is ligated together, then separating the reaction product, and then cyclically repeating the process until the sequence has been amplified to the desired degree. Detection may then be carried out in like manner as described above with respect to PCR.

Strand displacement amplification (SDA) is also carried out in accordance with know techniques. See: G. Walker, et al., *Proc. Nat'l. Acad. Sci. USA* 89:392–396 (1992); G. Walker et al., *Nucleic Acids Res.* 20:1691–1696(1992). SDA may be carried out with a single amplification primer or a pair of amplification primers, with exponential amplification being achieved with the latter. In general, SDA amplification primers comprise, in the 5' to 3' direction, a flanking sequence (the DNA sequence of which is noncritical), a restriction site for the restriction enzyme employed in the reaction, and an oligonucleotide sequence (e.g., oligonucleotide probe of the present invention) which hybridizes to the target sequence to be amplified and/or detected. The flanking sequence, which simply serves to facilitate binding of the restriction enzyme to the recognition site is preferably about 15 to 20 nucleotides in length; the restriction site is functional in the SDA reaction (i.e., phosphorothioate linkages incorporated into the primer strand do not inhibit subsequent nicking—a condition which may be satisfied through use of a nonpalindromic recognition site); the oligonucleotide probe portion is preferably about 13 to 15 nucleotides in length. SDA is carried out with a single amplification primer as follows: a restriction fragment (preferably about 50 to 100 nucleotides in length and preferably of low GC content) containing the sequence to be detected is prepared by digesting a DNA sample with one or more restriction enzymes, the SDA amplification primer is added to a reaction mixture containing the restriction fragment so that a duplex between the restriction fragment and the amplification primer is formed with a 5' overhang at each end, a restriction enzyme which binds to the restriction site on the amplification probe (e.g., HincII) is added to the reaction mixture, an exonuclease deficient DNA polymerase (e.g. an exonuclease deficient form of *E. coli* DNA polymerase I, See: V. Derbyshire, *Science* 240:199–201 (1988)) is added to the reaction mixture, and three dNTPs and one dNTP[αS], with the dNTP[αS] selected so that a phosphorothioate linkage is incorporated into the primer strand at the restriction site for the particular restriction enzyme employed (e.g., dGTP, dCTP, dTTP, and dATP[αS] when the restriction enzyme is HincII) are added to the reaction mixture. The DNA polymerase extends the 3' ends of the duplex with the dNTPs to form a downstream complement of the target strand, the restriction enzyme nicks the restriction site on the amplification primer, and the DNA polymerase extends the 3' end of the amplification primer at the nick to displace the previously formed downstream complement of the target strand. The process is inherently repetitive because the restriction enzyme continuously nicks new complementary strands as they are formed from the restriction site, and the DNA polmerase continuously forms new complementary strands from the nicked restriction site. SDA can be carried out with a pair of primers on a double stranded target DNA sequence, with the second primer binding to the 5' end of the complementary strand, so that two sets of repetitive reactions are occurring simultaneously, with the process proceeding exponentially because the products of one set of reactions serve as target for the amplification primer in the other set of reactions. In addition, the step of first digesting the DNA sample to form a restriction fragment can be eliminated by exploiting the strand displacing activity of the DNA polymerase and adding a pair of "bumper" primers which bind to the substrate at a flanking position 5' to the position at which each amplification primer binds. Each bumper primer extension product displaces the corresponding amplification primer extension product, and the two displaced, complementary, amplification primer extension products bind to one another to form a double-stranded DNA fragment which can the serve as a substrate for exponential SDA with that pair of SDA primers.

When SDA is employed, the oligonucleotide probes of the invention are preferably selected so that guanine plus cytosine content is low, preferably comprising less than 70% of the total nucleotide composition of the probe. Similarly, the target sequence should be of low GC content to avoid the formation of secondary structures.

A kit for detecting mutant EOAD gene nucleic acid in a nucleic acid sample contains at least one probe fragment derived from a sequence of the present invention, and hybridization solution for enabling hybridization between the probe or probes and the nucleic acid sample, with the probe either suspended in the solution or provided separately in lyophilized form. One example of a suitable hybridization solution is a solution comprised of 6×SSC (0.9M sodium chloride. 0.09M sodium citrate, pH 7.0), 0.1M EDTA pH 8.0, 5×Denhardt's solution [0.1% (w/v) Ficoll Type 400, 0.1% (w/v) polyvinylpyrrolidone, 0.1% (w/v) bovine serum albumin], and 100 µg/ml sheared, denature salmon sperm DNA, commercially available from Bethesda Research Laboratories, Gaithersburg, Md. 20877 USA under Catalog No. 5565UA. See also T. Maniatis et al., *Molecular Cloning: A Laboratory Manual*, 387–388 (1982)(Cold Spring Harbor Laboratory). The components of the kit are packaged together in a common container (e.g., a container sealed with a frangible seal), the kit typically including an instruction sheet for carrying out a specific embodiment of the method of the present invention. Additional optional components of the kit, depending on the assay format to be employed, include a second probe for carrying out PCR as explained above (or, in the case of a kit for carrying out a detecting step (e.g., a probe of the invention labeled with a detectable marker and optionally an enzyme substrate when the detectable marker is an enzyme).

The polypeptides having the amino acid sequence depicted in FIGS. 1 (SEQ ID NO:2) and 2 (SEQ ID NO:4), their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, *Nature*, 256:495–497), the trioma technique, the human B-cell hybridoma technique (Kozbor et al., 1983, *Immunology Today* 4:72), and the EBV-hybridoma technique to produce human monoclonal antibodies (Cole, et al., 1985, in *Monoclonal Antibodies and Cancer Therapy*, Alan R. Liss, Inc., pp. 77–96).

Techniques described for the production of single chain antibodies (U.S. Pat. No. 4,946,778) can be adapted to produce single chain antibodies to immunogenic polypeptide products of this invention.

A kit for detecting mutant EOAD protein in a protein sample contains at least one antibody against a polypetide of the present invention, and protein binding solution for enabling binding between the antibody and the polypeptide sample, with the antibody either suspended in the solution or provided separately in lyophilized form.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clones to a metaphase chromosomal spread can be used to provide a precise chromosomal location in one step. This technique can be used with cDNA as short as 500 or 600 bases; however, clones larger than 2,000 bp have a higher likelihood of binding to a unique chromosomal location with sufficient signal intensity for simple detection. FISH requires use of the clones from which the EST was derived, and the longer the better. For example, 2,000 bp is preferred, 4,000 is more preferred, and more than 4,000 is probably not necessary to get good results a reasonable percentage of the time. For a review of this technique, see Verma et al., *Human*

Chromosomes: A Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Comparison of affected and unaffected individuals generally involves first looking for structural alterations in the chromosomes, such as deletions or translocations that are visible from chromosome spreads or detectable using PCR based on that cDNA sequence. Ultimately, complete sequencing of genes from several individuals is required to confirm the presence of a mutation and to distinguish mutations from polymorphisms. Skilled artisans can readily obtain the EOAD gene from normal human individuals using the nucleotide and amino acid sequences of the invention. Mutants of the gene can be determined by comparison of the normal sequence to that gene sequence derived from individuals with EOAD using the nucleotide and amino acid sequences of the invention.

All methods, compositions and kits disclosed herein relating to the EOAD gene are also useful with any EOAD splice variants.

EXAMPLES

Example 1

EOAD Gene Expression from DNA Sequences Corresponding to EOAD ESTs

An EOAD gene sequence of the present invention coding part of a human EOAD gene product is introduced into an expression vector using conventional technology. (Techniques to transfer cloned sequences into expression vectors that direct protein translation in mammalian, yeast, insect or bacterial expression systems are well known in the art.) Commercially available vectors and expression systems are available from a variety of suppliers including Stratagene (La Jolla, Calif.), Promega (Madison, Wis.), and Invitrogen (San Diego, Calif.). If desired, to enhance expression and facilitate proper protein folding, the codon context and codon expressing organism, as explained by Hatfield, et al., U.S. Pat. No. 5,082,767, incorporated herein by this reference.

The following is provided as one exemplary method to generate polypeptide(s) from cloned EOAD cDNA sequence (s) which include the coding region for the peptide of interest and which EOAD cDNA sequences are obtained by use of an EST of the present invention, as hereinabove described. For EOAD cDNA sequences lacking a poly A sequences, this sequence can be added to the construct by, for example, splicing out the poly A sequence from pSG5 (Stratagene) using BglII and SalI restriction endonuclease enzymes and incorporating it into the mammalian expression vector pXT1 (Stratagene). pXT1 contains the LTRs and a portion of the gag gene from Moloney Murine Leukemia Virus. The position of the LTRS in the construct allow efficient stable transfection. The vector includes the Herpes Simplex thymidine kinase promoter and the selectable neomycin gene. The EOAD cDNA is obtained by PCR from the bacterial vector using oligonucleotide primers complementary to the cDNA and containing restriction endonuclease sequences for PstI in corporated into the 5' primer and BglII at the 5' end of the corresponding cDNA 3' primer, taking care to ensure that the cDNA is positioned such that its followed with the poly A sequence. The purified fragment obtained from the resulting PCR reaction is digested with PstI, blunt ended with an exonuclease, digested with BglII, purified and ligated to pXT1, now containing a poly A sequence and digested BglII.

The ligated product is transfected into mouse NIH 3T3 cells using Lipofectin (Life Technologies, Inc., Grand, Island, N.Y.) under conditions outlined in the product specification. Positive transfectants are selected after growing the transfected cells in 600 ug/ml G418 (Sigma, St. Louis, Mo.). The protein is preferably released into the supernatant. However, it the protein has membrane binding domains, the protein may additionally be retained within the cell or expression may be restricted to the cell surface.

Since it may be necessary to purify and locate the transfected product, synthetic 15-mer peptides synthesized form the predicted cDNA sequences are injected into mice to generate antibody to the polypeptide encoded by the cDNA.

A method to make antibody production possible, the EOAD cDNA sequence is additionally incorporated into eukaryotic expression vectors and expressed as a chimeric with, for example, β-globin. Anti body to β-globin is used to purify the chimeric. Corresponding protease cleavage sites engineered between the β-globin gene and the cDNA are then used to separate the two polypeptide fragments form one another after translation. A useful expression vector for generating β-globin chimerics is pSG5 (Stratagene). This vector encodes rabbit β-globin. Intron II of the rabbit β-globin gene facilitates splicing of the expressed transcript, and the polyadenylation signal incorporated into the construct increases the level of expression. These techniques as described are well known to those skilled in the art of molecular biology. Standard methods are published in methods texts such as David et al. and many of the methods are available form the technical assistance representatives from Stratagene, Life Technologies, Inc., or Promega. Polypeptide may additionally be produced from either construct using in vitro translation systems such as In vitro Express™ translation Kit. (Stratagene).

Example 2

Production of an Antibody to a Human EOAD Protein

Substantially pure protein or polypeptide is isolated from the transfected or transformed cells using methods known in the art or described herein. The protein can also be produced in a recombinant prokaryotic expression system, such as E. coli, or can be chemically synthesized. Concentration of protein in the final preparation is adjusted, for example, by concentration on an Amicon filter device, to the level of a few micrograms/ml. Monoclonal or polyclonal antibody to the protein can then be prepared as known in the art or described in the following paragraph.

Monoclonal antibody to epitopes of any of the peptides identified and isolated as described can be prepared from murine hybridomas according to the classical method of Kohler, G. and Milstein, C., Nature, 256:495 (1975) or modifications of the methods thereof. Briefly, a mouse is repetitively inoculated with a few micrograms of the selected protein over a period of a few weeks. The mouse is then sacrificed, and the antibody producing cells of the spleen isolated. The spleen cells are fused by means of polyethylene glycol with mouse myeloma cells, and the excess unfused cells destroyed by growth of the system on selective medis comprising aminopterin (HAT media). The successfully fused cells are diluted and aliquots of the dilution placed in wells of a microtiter plate where growth o the culture is continued. Anti body producing clones are identified by detection of antibody in the supernatant fluid of the wells by immunoassay procedures, such as ELISA, as originally described by Engvall, E., *Meth. Enzymol.*, 70:419 (1980), and modified methods thereof. Selected positive clones can be expanded and their monoclonal antibody product harvested for use. Detailed procedures for monoclonal anti body production are described in Davis, L. et al. *Basic Methods in Molecular Biology Elsvier*, New York. Section 21-2 (1986).

What is claimed is:

1. An isolated polynucleotide comprising a polynucleotide that encodes the polypeptide sequence of SEQ ID NO:4.

2. An expression vector comprising cis-acting control elements effective for expression in a host cell of an operatively linked polynucleotide according to claim 1.

3. A host cell having expressibly incorporated therein an expression vector according to claim 2.

4. A process for making a polypeptide having the amino acid sequence of SEQ ID NO:4, comprising expressing in a host cell a polynucleotide according to claim 1 under conditions sufficient for the production of said polypeptide, and wherein said polypeptide is produced and isolated from said cell.

5. An isolated polynucleotide comprising the sequence of the human cDNA in ATCC Deposit No.: 97238.

6. An isolated polynucleotide comprising the polynucleotide sequence of SEQ ID NO: 3 which encodes the polypeptide of SEQ ID NO:4.

7. An isolated polynucleotide which is the polynucleotide of SEQ ID NO:3.

8. An isolated polynucleotide comprising the entire RNA transcript of SEQ ID NO:3.

9. An isolated polynucleotide comprising a polynucleotide sequence which is complementary to the polynucleotide of any one of claims 1, 5, 6, or 7, the entire length of said polynucleotide set or their in such claim.

10. An isolated polynucleotide comprising the isolated polynucleotide of any one of claims 1, 5, 6, or 7, or their complementary sequences, which is DNA or RNA.

* * * * *